US011622560B2

(12) United States Patent
Zhang et al.

(10) Patent No.: US 11,622,560 B2
(45) Date of Patent: Apr. 11, 2023

(54) MYROIDES ODORATIMIMUS BIOCONTROL STRAIN FOR EFFICIENTLY DEGRADING AFLATOXIN AND APPLICATION THEREOF

(71) Applicant: OIL CROPS RESEARCH INSTITUTE, CHINESE ACADEMY OF AGRICULTURAL SCIENCES, Hubei (CN)

(72) Inventors: Qi Zhang, Hubei (CN); Peiwu Li, Hubei (CN); Tong Wang, Hubei (CN); Xiaoxia Ding, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 208 days.

(21) Appl. No.: 16/886,791

(22) Filed: May 29, 2020

(65) Prior Publication Data

US 2020/0291491 A1 Sep. 17, 2020

Related U.S. Application Data

(63) Continuation-in-part of application No. PCT/CN2018/118204, filed on Nov. 29, 2018.

(30) Foreign Application Priority Data

Nov. 29, 2017 (CN) ........................ 201711225506.2
Nov. 23, 2018 (CN) ........................ 201811409668.6

(51) Int. Cl.

| | |
|---|---|
| ***A01N 63/20*** | (2020.01) |
| ***C12N 1/20*** | (2006.01) |
| *A23L 5/20* | (2016.01) |
| *C12R 1/01* | (2006.01) |

(52) U.S. Cl.
CPC ............... *A01N 63/20* (2020.01); *C12N 1/20* (2013.01); *C12N 1/205* (2021.05); *A23L 5/28* (2016.08); *C12R 2001/01* (2021.05)

(58) Field of Classification Search
CPC .......... A01N 63/20; C12N 1/20; C12N 1/205; A23L 5/28; C12R 2001/01
See application file for complete search history.

(56) References Cited

U.S. PATENT DOCUMENTS

2011/0135796 A1 6/2011 Chang
2015/0230460 A1 * 8/2015 Schook .................... C02F 1/50
514/616

FOREIGN PATENT DOCUMENTS

| | | | | |
|---|---|---|---|---|
| CN | 102031234 | | 4/2011 | |
| CN | 102146350 A | * | 8/2011 | |
| CN | 103756932 A | * | 4/2014 | |
| CN | 103981132 | | 8/2014 | |
| CN | 103981135 | | 8/2014 | |
| CN | 106065396 | | 11/2016 | |
| CN | 106381277 | | 2/2017 | |
| CN | 107201322 | | 9/2017 | |
| WO | WO-2009140215 A2 | * | 11/2009 | ............ A61K 31/47 |

OTHER PUBLICATIONS

CN 102146350. Aug. 10, 2011. English abstract. (Year: 2011).*
Chourasia, HK. Kernel infection and aflatoxin production in peanut (*Arachis hypogaea* L.) by Aspergillus flavus in presence of geocarposphere bacteria. J. Food. Sci. Technol. 1995. 32(6): 459-464. (Year: 1995).*
Vancanneyt, M et al. Reclassification of Flavobacterium odoratum (Stutzer 1929) strains to a new genus, *Myroides*, as *Myroides odoratus* comb. nov. and *Myroides odoratimimus* sp. nov. International Journal of Systematic Bacteriology. 1996. 46(4): 926-932. (Year: 1996).*
Licker, M et al. Extensively drug-resistant Myroides odoratimimus—a case series of urinary tract infections in immunocompromised patients. Infection and Drug Resistance. 2018. 11: 743-749. (Year: 2018).*
K.Raksha Rao et al., "Biological detoxification of Aflatoxin B1 by Bacillus licheniformis CFR1," Food Control, vol. 71, Jun. 28, 2016, pp. 234-241.
Shu Guan, "Isolation, Screening, Identification of Aflatoxin B1, Trichochecene Mycotoxins Detoxification Microorgnisms and The Mechanisms," Dissertation of Doctoral Degree, China Agricultural University, Jun. 2009, pp. 1-10.

* cited by examiner

*Primary Examiner* — Renee Claytor
*Assistant Examiner* — Susan E. Fernandez
(74) *Attorney, Agent, or Firm* — JCIP Global Inc.

(57) ABSTRACT

The invention belongs to the field of microbes and specifically relates to a myroides odoratimimus biocontrol strain for efficiently degrading aflatoxin and an application thereof. A myroides odoratimimus biocontrol strain 3J2MO is preserved at the China Center for Type Culture Collection (referred to as CCTCC) on Jun. 13, 2017 with preservation number CCTCC No. M 2017329. The myroides odoratimimus biocontrol strain of the invention can effectively degrade aflatoxin and may be configured to degrade aflatoxin and treat aflatoxin pollution of food crops.

12 Claims, No Drawings

MYROIDES ODORATIMIMUS BIOCONTROL STRAIN FOR EFFICIENTLY DEGRADING AFLATOXIN AND APPLICATION THEREOF

CROSS-REFERENCE TO RELATED APPLICATION

This application is a continuation-in-part application of International Application number PCT/CN2018/118204, filed on Nov. 29, 2018, which claims the priority benefit of China Patent Application No. 201711225506.2, filed on Nov. 29, 2017, and China Patent Application No. 201811409668.6, filed on Nov. 23, 2018. The entirety of each of the above-mentioned patent applications is hereby incorporated by reference herein and made a part of this specification.

BACKGROUND

Technical Field

The disclosure belongs to the field of microbes and specifically relates to a myroides odoratimimus biocontrol strain for efficiently degrading aflatoxin and an application thereof.

Description of Related Art

Aspergillus flavus is a pathogenic fungus that can produce a type of strongly carcinogenic and highly toxic fungal toxin, aflatoxin, including B, G, and M families, wherein B1 is the most common and the most toxic. Aflatoxin may widely pollute food crops such as peanuts, corn, etc. and seriously threaten the health of human and livestock, causing great economic losses. Therefore, it is urgent to strengthen the treatment of Aspergillus flavus and toxin pollution.

The traditional methods of removing aflatoxin B1 (AFB1) mainly include adsorption, extraction, heat treatment, radiation treatment, acid-base treatment, and redox treatment, which are sometimes time and effort consuming, have low detoxification rate, and may easily cause the loss of nutrients. However, the biological method has the advantages of safety, high efficiency, and lasting. Therefore, it is of great significance for the agricultural industry and economic benefits of China to strengthen the research on aflatoxin biological treatment.

Bacterial and metabolite biodegradation of aflatoxin is not widely reported. Stenotrophomonas maltophilia screened by cumoric medium as applied by Guan Shu, Li Junxia, et al. can degrade aflatoxin with a degradation rate of 82.5%. Wang Ning et al. studied an orange-red myxococcus strain from gray langur feces and discovered that the degradation rate of AFB1 is 78.2% under the optimal culture conditions. In the prior art, there have been no reports of the use of myroides odoratimimus to degrade aflatoxin.

SUMMARY

The technical problem to be solved by the invention is to provide a myroides odoratimimus biocontrol strain 3J2MO for efficiently degrading aflatoxin and an application thereof in view of the deficiencies of the prior art. The myroides odoratimimus biocontrol strain 3J2MO in the invention can significantly degrade aflatoxin.

In order to solve the above technical problem, the technical solution adopted by the invention is as follows:

The myroides odoratimimus biocontrol strain 3J2MO was preserved at the China Center for Type Culture Collection (referred to as CCTCC) on Jun. 13, 2017 with preservation address: Wuhan University, Wuhan, China and preservation number CCTCC No. M 2017329.

In the invention, 100 μL of the soil after gradient dilution collected from the peanut field in Huangpi, Hubei is smeared in a lysogeny broth (LB) solid culture medium for culturing. Grown bacteria are selected with an inoculating loop and transferred to a fresh LB solid culture medium for streak plate. A single colony is selected after multiple transfers. A strain 3J2MO with significant degradation effect on aflatoxin is screened through the aflatoxin degradation experiment and is preserved at the China Center for Type Culture Collection (referred to as CCTCC) with preservation address: Wuhan University, Wuhan, China and preservation number CCTCC No. M 2017329. The type of the strain is identified using 16S rDNA specificity amplification technology combined with morphological characteristics, and physiological and biochemical experiments. The result shows that the strain is a myroides odoratimimus strain, belonging to actinomycetes, brevibacterium.

TABLE 1

Main biological characteristics of myroides odoratimimus 3J2MO:

| Gram stain | Oxygen | Spore | Catalase | Culture temperature | Culture time | MR test | Nitrate reduction | Catalase | Acid-fast stain |
|---|---|---|---|---|---|---|---|---|---|
| Positive | Facultative anaerobic | Not formed | Positive | 20-30° C. | 12-24 hours | Positive | Positive | Positive | Negative |

The application of the myroides odoratimimus biocontrol strain 3J2MO in degradation of aflatoxin or in prevention and control of toxin production by Aspergillus flavus is provided.

A preparation for degrading aflatoxin is provided, which includes a ferment of the myroides odoratimimus 3J2MO.

According to the solution, the preparation form of the preparation is liquid, spraying powder, dry wettable powder, or dry wettable granule. The preparation may be obtained by preparing the ferment of myroides odoratimimus 3J2MO and a biologically acceptable auxiliary material. For example, a mixture of peanut meal and LB liquid culture medium (mass volume ratio may be selected as 6:4) may be adopted as the auxiliary material; a mixture of corn meal and LB liquid culture medium (mass volume ratio may be selected as 5:5) may be adopted as the auxiliary material; or cassava meal, sugar cane meal, etc. (containing about 10% humus and a small amount of microelements) may be adopted as the auxiliary material.

According to the solution, the preparation is liquid and the final concentration of myroides odoratimimus 3J2MO in the preparation is (1-9)×$10^7$ CFU/mL.

According to the solution, the preparation is a fermentation broth of myroides odoratimimus 3J2MO and the final concentration of myroides odoratimimus 3J2MO in the fermentation broth of myroides odoratimimus 3J2MO is $(1\text{-}9)\times10^7$ CFU/mL.

According to the solution, the preparation method of the fermentation broth of myroides odoratimimus 3J2MO is as follows. Myroides odoratimimus 3J2MO is activated in an LB plate and cultured in an incubator at 28° C. for 24 hours. A single colony of myroides odoratimimus is selected with a needle, transferred to a LB liquid culture medium, and shaking cultured for 12 hours to 24 hours. 1% to 3% of a culture broth is absorbed, transferred to a fresh LB liquid culture medium, and shaking cultured for 12 hours to 4 hours to obtain a fermentation broth of an antagonize strain of myroides odoratimimus 3J2MO.

A method for degrading aflatoxin is provided and the specific application method is as follows. A preparation for degrading aflatoxin is coated or sprayed onto the surface of a biological sample or mixed with the biological sample for degradation of aflatoxin to prevent and cure aflatoxin pollution of the biological sample.

According to the solution, the aflatoxin includes aflatoxin B1, aflatoxin B2, aflatoxin G1, aflatoxin G2, and aflatoxin M1.

A method for preventing and controlling toxin production by Aspergillus flavus is provided and the specific application method is as follows. A preparation for degrading aflatoxin is coated on the surface of a biological sample or mixed with the biological sample for prevention and control of toxin production by Aspergillus flavus to prevent aflatoxin pollution of the biological sample.

According to the solution, the aflatoxin includes aflatoxin B1, aflatoxin B2, aflatoxin G1, aflatoxin G2, and aflatoxin M1.

The beneficial effects of the invention:

The invention provides the myroides odoratimimus strain 3J2MO with good degradation effect on aflatoxin for the first time. The strain may be used to degrade aflatoxin, to prevent and control toxin production by Aspergillus flavus, and to treat biological samples. The biological samples may be peanuts and processed products thereof, corn and processed products thereof, animal feed, other agricultural products and processed products thereof susceptible to molding, etc., but are not limited thereto.

DETAILED DESCRIPTION OF DISCLOSED EMBODIMENTS

In the invention, 100 μL of the soil after gradient dilution collected from the peanut field in Huangpi, Hubei is smeared in a lysogeny broth (LB) solid culture medium for culturing. Grown bacteria are selected with an inoculating loop and transferred to a fresh LB solid culture medium for streak plate. A single colony is selected after multiple transfers. A strain 3J2MO with significant degradation effect on aflatoxin is screened through the aflatoxin degradation experiment and is preserved at the China Center for Type Culture Collection (referred to as CCTCC) with preservation number CCTCC No. M 2017329.

The specific process of obtaining a myroides odoratimimus strain 3J2MO with significant degradation effect on aflatoxin by screening through the aflatoxin degradation experiment is as follows. The aflatoxin degradation experiment is performed on the single colony selected above to obtain a myroides odoratimimus strain having a relatively high degradation rate of more than 80% on aflatoxin. The Myroides odoratimimus is cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 $r\cdot min^{-1}$ for 12 hours. 1% of a culture broth is absorbed, transferred to a triangular flask containing 15 mL of LB liquid culture medium, and shaking cultured at 28° C. and 200 $r\cdot min^{-1}$ for 12 hours to obtain a fermentation broth of an antagonize strain. An aflatoxin B2 is added to the fermentation broth of myroides odoratimimus (the final concentration is $1\times10^7$ CFU/mL), which is then cultured together in the LB culture medium at 28° C. and 200 rpm for 5 days. The initial concentration of aflatoxin is about 100 μg/mL. Then, a conventional bacterial method is used to separate the myroides odoratimimus strain. A strain with a higher degradation rate on aflatoxin is selected from each strain by the aflatoxin degradation experiment. The experiment of culturing together with aflatoxin above is repeated for more than 3 years with at least more than 20 cycles until the efficiency of myroides odoratimimus degrading aflatoxin obtained is more than 90%. Finally, an artificially domesticated myroides odoratimimus 3J2MO is obtained.

Embodiment 1

1) Myroides odoratimimus 3J2MO is activated in an LB plate and cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 $r\cdot min^{-1}$ for 12 hours. 1% of a culture broth is absorbed, transferred to a triangular flask containing 15 mL of LB liquid culture medium, and shaking cultured at 28° C. and 200 $r\cdot min^{-1}$ for 12 hours to obtain a fermentation broth of an antagonize strain.

2) An aflatoxin B1 standard solution is added to a fermentation broth of myroides odoratimimus (with final concentration of $1\times10^7$ CFU/mL) to be cultured in the LB culture medium together at 28° C. and 200 rpm for 5 days with 3 repetitions per treatment.

3) The content of aflatoxin B1 in the culture broth is measured (Table 2).

TABLE 2

Degradation effect of biocontrol bacteria on aflatoxin

| Treatment | AFB1 | AFB1 + CCTCC No. M 20177329 |
|---|---|---|
| AFB1 toxin content (ng/ml) | 39.69 ± 3.90 | 1.61 ± 0.16 |

It can be seen from the experimental result that the degradation rate of the myroides odoratimimus strain CCTCC No. M 2017329 on aflatoxin is about 95.61%, indicating that the strain has the ability to degrade aflatoxin.

Embodiment 2

Peanut grains obtained from Hubei peanut field are ground into powder and 0.5 g of peanut powder is weighed into a petri dish. 500 μL of spore solution of toxin-producing Aspergillus flavus ($5\times10^5$/mL) is added and cultured in an incubator at 28° C. for 7 days.

A fermentation broth of 500 μL of CCTCC No. M 20177329 strain is added to the peanut powder filled with spores, the same amount of LB culture medium is used as a control, and cultured in the culture medium at 28° C. for 5 days with 3 repetitions in the experiment.

15 mL of 70% methanol water is added and placed in a shaker for 30 minutes after vortex. 8 mL of ultrapure water is added to 3 mL of supernatant to vortex and centrifuge;

8 mL of supernatant is taken and the content of aflatoxin B1 is determined using immunoaffinity column, high-performance liquid chromatography (HPLC) method (Table 3), with 3 repetitions in the experiment.

TABLE 3

Treatment effect of biocontrol bacteria on Aspergillus flavus polluted peanut

| Treatment | AFB1 | AFB1 + CCTCC No. M 20177329 |
|---|---|---|
| AFB1 toxin content (ng/ml) | 111.68 ± 9.05 | 1.39 ± 0.36 |

It can be seen from the experimental result that the prevention and control rate of CCTCC No. M 2017329 grain on toxin production by Aspergillus flavus on peanut is about 98.76%, indicating that the strain has a good treatment effect on Aspergillus flavus polluted peanut.

Embodiment 3

1) Myroides odoratimimus 3J2MO is activated in an LB plate and cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 r·min$^{-1}$ for 12 hours. 1% of a culture broth is absorbed, transferred to a triangular flask containing 15 mL of LB liquid culture medium, and shaking cultured at 28° C. and 200 r·min$^{-1}$ for 12 hours to obtain a fermentation broth of an antagonize strain.

2) An aflatoxin B2 standard solution is added to a fermentation broth of myroides odoratimimus (with final concentration of 1×10$^7$ CFU/mL) to be cultured in the LB culture medium together at 28° C. and 200 rpm for 5 days with 3 repetitions per treatment.

3) The final content of aflatoxin B2 in the culture medium is measured and the degradation rate is calculated.

After calculation of the experimental result, the degradation rate of the myroides odoratimimus CCTCC No. M2017329 strain on aflatoxin B2 is 96.23%, indicating that the strain has the ability to degrade aflatoxin B2.

Embodiment 4

1) Myroides odoratimimus 3J2MO is activated in an LB plate and cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 r·min$^{-1}$ for 12 hours. 1% of a culture broth is absorbed, transferred to a triangular flask containing 15 mL of LB liquid culture medium, and shaking cultured at 28° C. and 200 r·min$^{-1}$ for 12 hours to obtain a fermentation broth of an antagonize strain.

2) An aflatoxin G1 standard solution is added to the fermentation broth of myroides odoratimimus (with final concentration of 1×10$^7$ CFU/mL) to be cultured in the LB culture medium together at 28° C. and 200 rpm for 5 days with 3 repetitions per treatment.

3) The final content of aflatoxin G1 in the culture medium is measured and the degradation rate is calculated.

After calculation of the experimental result, the degradation rate of the myroides odoratimimus CCTCC No. M2017329 strain on aflatoxin G1 is 96.73%, indicating that the strain has the ability to degrade aflatoxin G1.

Embodiment 5

1) Myroides odoratimimus 3J2MO is activated in an LB plate and cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 r·min$^{-1}$ for 12 hours. 1% of a culture broth is absorbed, transferred to a triangular flask containing 15 mL of LB liquid culture medium, and shaking cultured at 28° C. and 200 r·min$^{-1}$ for 12 hours to obtain a fermentation broth of an antagonize strain.

2) An aflatoxin G2 standard solution is added to the fermentation broth of myroides odoratimimus (with final concentration of 1×10$^7$ CFU/mL) to be cultured in the LB culture medium together at 28° C. and 200 rpm for 5 days with 3 repetitions per treatment.

3) The final content of aflatoxin G2 in the culture medium is measured and the degradation rate is calculated.

After calculation of the experimental result, the degradation rate of the myroides odoratimimus CCTCC No. M2017329 strain on aflatoxin G2 is 97.55%, indicating that the strain has the ability to degrade aflatoxin G2.

Embodiment 6

1) Myroides odoratimimus 3J2MO is activated in an LB plate and cultured in an incubator at 28° C. for 24 hours. A single colony of activated myroides odoratimimus is selected with a needle, transferred to a triangular flask containing 15 mL of LB liquid culture medium, and shaking cultured at 28° C. and 200 r·min$^{-1}$ for 12 hours. 1% of a culture broth is absorbed, transferred to a triangular flask containing 15 mL of LB liquid culture medium, and shaking cultured at 28° C. and 200 r·min$^{-1}$ for 12 hours to obtain a fermentation broth of an antagonize strain.

2) An aflatoxin M1 standard solution is added to the fermentation broth of myroides odoratimimus (with final concentration of 1×10$^7$ CFU/mL) to be cultured in the LB culture medium together at 28° C. and 200 rpm for 5 days with 3 repetitions per treatment.

3) The final content of aflatoxin M1 in the culture medium is measured and the degradation rate is calculated.

After calculation of the experimental result, the degradation rate of the myroides odoratimimus CCTCC No. M2017329 strain on aflatoxin M1 is 97.55%, indicating that the strain has the ability to degrade aflatoxin M1.

Embodiment 7

The same method as Patent Document CN 105925513 A is adopted. The degradation effects of flavobacterium with preservation number CICC 20907 in the patent document and the myroides odoratimimus CCTCC No. M2017329 strain of the present invention on aflatoxin B1 are compared. The comparison results are shown in Table 4. The results show that the degradability of myroides odoratimimus CCTCC No. M2017329 on aflatoxin B1 provided by the present invention far exceeds the degradability of flavobacterium CICC 20907 on aflatoxin B1 in Patent Document CN 105925513 A.

TABLE 4

| Comparison of degradability of present invention and flavobacterium CICC 20907 strain in Patent 105925513 A on aflatoxin B1 | |
|---|---|
| Degradation rate of myroides odoratimimus CCTCC No. M2017329 on aflatoxin B1 | Degradation rate of flavobacterium CICC 20907 on aflatoxin B1 in Patent CN 105925513 A |
| Test 1: 97.2% | Embodiment 1: 45.7% |
| Test 2: 98.3% | Embodiment 2: 46.7% |
| Test 3: 97.1% | Embodiment 3: 45.8% |
| Test 4: 96.7% | Embodiment 4: 47.1% |

Combining Embodiments 1, 2, 3, 4, 5, 6, and 7, the myroides odoratimimus CCTCC No. M2017329 strain of the invention has very strong degradability on all five types of common aflatoxins: aflatoxin B1, aflatoxin B2, aflatoxin G1, aflatoxin G2, and aflatoxin M1. After researching domestic and foreign citations, a strain with such strong degradability on five types of common aflatoxins has not been reported domestically and abroad.

What is claimed is:

1. A method for degrading aflatoxin, wherein a preparation for degrading aflatoxin is coated or sprayed onto a surface of a biological sample or mixed with the biological sample for degradation of aflatoxin, wherein the preparation comprises a fermented product of a Myroides odoratimimus biocontrol strain 3J2MO comprising the cells of the strain, and the myroides odoratimimus Myroides odoratimimus biocontrol strain 3J2MO is preserved at the China Center for Type Culture Collection (referred to as CCTCC) on Jun. 13, 2017 with preservation number CCTCC No. M 2017329.

2. The method according to claim 1, wherein the aflatoxin comprises aflatoxin B1, aflatoxin B2, aflatoxin G1, aflatoxin G2, and aflatoxin M1.

3. A method for degrading aflatoxin, wherein a preparation for degrading aflatoxin is coated or sprayed onto a surface of a biological sample or mixed with the biological sample for degradation of aflatoxin, wherein the preparation comprises a fermented product of Myroides odoratimimus biocontrol strain 3J2MO comprising the cells of the strain, and the preparation form of the preparation is a liquid, spraying powder, dry wettable powder, or dry wettable granule.

4. A method for degrading aflatoxin, wherein a preparation for degrading aflatoxin is coated or sprayed onto a surface of a biological sample or mixed with the biological sample for degradation of aflatoxin, wherein the preparation comprises a fermented product of Myroides odoratimimus biocontrol strain 3J2MO comprising the cells of the strain, the preparation is liquid, and the final concentration of the Myroides odoratimimus biocontrol strain 3J2MO in the preparation is $1\times10^7$ CFU/mL to $9\times10^7$ CFU/mL.

5. A method for degrading aflatoxin, wherein a preparation for degrading aflatoxin is coated or sprayed onto a surface of a biological sample or mixed with the biological sample for degradation of aflatoxin, wherein the preparation comprises a fermented product of Myroides odoratimimus biocontrol strain 3J2MO comprising the cells of the strain, the preparation is a fermentation broth of Myroides odoratimimus 3J2MO, and the final concentration of Myroides odoratimimus 3J2MO in the fermentation broth is $1\times10^7$ CFU/mL to $9\times10^7$ CFU/mL.

6. The method for degrading aflatoxin of claim 5, wherein the preparation method of the fermentation broth of the Myroides odoratimimus biocontrol strain 3J2MO is:

culturing the Myroides odoratimimus biocontrol strain 3J2MO in a lysogeny broth (LB) plate in an incubator at 28° C. for 24 hours; selecting a single colony of Myroides odoratimimus with a needle, transferring the single colony to a liquid culture medium, and performing a shaking culture for 12 hours to 24 hours; transferring 1% to 3% of the resulting culture broth comprising Myroides odoratimimus to a fresh LB liquid culture medium and performing a shaking culture for 12 hours to 24 hours; obtaining the fermentation broth of the Myroides odoratimimus 3J2MO.

7. A method for inhibiting aflatoxin production by Aspergillus flavus, wherein a preparation for degrading aflatoxin is coated on a surface of a biological sample or mixed with the biological sample for control of aflatoxin production by Aspergillus flavus to decrease aflatoxin pollution of the biological sample, wherein the preparation comprises a fermented product of Myroides odoratimimus biocontrol strain 3J2MO comprising the cells of the strain.

8. The method according to claim 7, wherein the aflatoxin comprises aflatoxin B1, aflatoxin B2, aflatoxin G1, aflatoxin G2, and aflatoxin M1.

9. A method for inhibiting aflatoxin production by Aspergillus flavus, wherein a preparation for degrading aflatoxin is coated on a surface of a biological sample or mixed with the biological sample for control of aflatoxin production by Aspergillus flavus to decrease aflatoxin pollution of the biological sample, wherein the preparation comprises a fermented product of Myroides odoratimimus biocontrol strain 3J2MO comprising the cells of the strain, and the preparation form of the preparation is a liquid, spraying powder, dry wettable powder, or dry wettable granule.

10. A method for inhibiting aflatoxin production by Aspergillus flavus, wherein a preparation for degrading aflatoxin is coated on a surface of a biological sample or mixed with the biological sample for control of aflatoxin production by Aspergillus flavus to decrease aflatoxin pollution of the biological sample, wherein the preparation comprises a fermented product of Myroides odoratimimus biocontrol strain 3J2MO comprising the cells of the strain, the preparation is liquid, and the final concentration of the Myroides odoratimimus biocontrol strain 3J2MO in the preparation is $1\times10^7$ CFU/mL to $9\times10^7$ CFU/mL.

11. A method for inhibiting aflatoxin production by Aspergillus flavus, wherein a preparation for degrading aflatoxin is coated on a surface of a biological sample or mixed with the biological sample for prevention and control of aflatoxin production by Aspergillus flavus to decrease aflatoxin pollution of the biological sample, wherein the preparation comprises a fermented product of Myroides odoratimimus biocontrol strain 3J2MO comprising the cells of the strain, the preparation is a fermentation broth of Myroides odoratimimus 3J2MO, and the final concentration of Myroides odoratimimus 3J2MO in the fermentation broth is $1\times10^7$ CFU/mL to $9\times10^7$ CFU/mL.

12. The method for inhibiting aflatoxin production by Aspergillus flavus of claim 11, wherein the preparation method of the fermentation broth of the Myroides odoratimimus biocontrol strain 3J2MO is:

culturing the Myroides odoratimimus biocontrol strain 3J2MO in a lysogeny broth (LB) plate in an incubator at 28° C. for 24 hours; selecting a single colony of Myroides odoratimimus with a needle, transferring the single colony to a liquid culture medium, and performing a shaking culture for 12 hours to 24 hours; transferring 1% to 3% of the resulting culture broth comprising Myroides odoratimimus to a fresh LB liquid culture medium and performing a shaking culture for 12 hours to 24 hours; obtaining the fermentation broth of the Myroides odoratimimus 3J2MO.

* * * * *